(12) United States Patent
Hidvegi et al.

(10) Patent No.: US 6,355,474 B1
(45) Date of Patent: Mar. 12, 2002

(54) IMMUNOSTIMULATORY AND METASTASIS INHIBITING FERMENTED VEGETAL MATERIAL

(76) Inventors: Mate Hidvegi, Hegedus Gy. u. 63, H-1133 Budapest; Rita Farkas Tomoskozine, Tarnoki ut 107, H-2030 Erd; Kaoly Lapis, Lonyai u. 25, H-1093 Budapest; Erzsebet Raso, Vanflia u. 60, H-1173 Budapest; Bela Szende, Ulloi ut 55, H-1091 Budapest, all of (HU)

( * ) Notice: Subject to any disclaimer, the term of this patent is extended or adjusted under 35 U.S.C. 154(b) by 0 days.

(21) Appl. No.: 09/485,221
(22) PCT Filed: Aug. 13, 1998
(86) PCT No.: PCT/HU98/00077
   § 371 Date: Mar. 28, 2000
   § 102(e) Date: Mar. 28, 2000
(87) PCT Pub. No.: WO99/08694
   PCT Pub. Date: Feb. 25, 1999

(30) Foreign Application Priority Data

Aug. 13, 1997 (HU) .............................. 9701392
Aug. 5, 1998 (HU) .............................. 9801797

(51) Int. Cl.$^7$ .............................. C12N 1/14; C12N 1/00
(52) U.S. Cl. .................. 435/254.21; 435/243
(58) Field of Search .......................... 426/18, 61, 650; 435/255.2, 174, 243, 244, 254.21

(56) References Cited

U.S. PATENT DOCUMENTS 5,702,943 A * 12/1997 Ehret

FOREIGN PATENT DOCUMENTS

EP         0684306 A1    11/1995
WO        WO 9220777     11/1992

OTHER PUBLICATIONS

Rompp: Chemical Encyclopedia, vol. 1, 537–538. Technical Publisher, Budapest, 1960, p. 538, lines 51–57.
Bandara et al., Phytochemistry, vol. 27, No. 1, pp. 225–226. 1988.
Helvetica Chimica Acta, vol. XXXIII.
DeVita, Jr., Cancer: Principles of Chermotherapy, Fourth Edition, vol. 1, 276–292.
Pethig et al., Proc. Natl. Acad. Sci., USA, vol. 81, pp. 2088–2091, Apr. 1984, Cell Biology.
Pethig et al., Proc. Natl. Acad. Sci., USA, vol. 82, pp. 1439–1442, Mar. 1985, Cell Biology.
Pethig et al., Proc. Natl. Acad. Sci., USA, vol. 80, pp. 129–132, Jan. 1983, Biochemistry.
Nishina et al., J. Agric. Food Chem., 1991, 39, 266–269.
Szent–Gyorgyi, Int. Journal of Quantum Chemistry: Quantum Biology Symposium, 9, 27–30, 1982.
Cosgrove et al., J. Chem. Soc. London, 4821–4823, 1952.
Szent–Gyorgyi, Int. Journal of Quantum Chemistry: Quantum Biology Symposium, 7, 217–222 (1980).
Szent–Gyorgyi, Int. Journal of Quantum Chemistry: Quantum Biology Symposium, 12, 257–261 (1985).
Tomoskozine Farkas et al., Margyar Kemiai Folyoirat, 102, evf. 1996. 7.sz.
Kang, K., Abstract of Kr 9 401 544 B, Feb. 24, 1994.
Kuo et al., Cytobios, vol. 81, No. 326, 1995, pp. 175–180.
Cosgrove et al. Isolation of Methoxy–and 2:6–Dimethoxy–p–Benzoquinone from Fermented Wheat Germ; Nature, vol. 169, pp. 966–967, 1952.*
Neufeldt et al. ed. Webster's New World Dictionary; Third Ed. pp. 499, 1988.*

* cited by examiner

Primary Examiner—Jon P. Weber
Assistant Examiner—Patricia Patten
(74) Attorney, Agent, or Firm—Birch, Stewart, Kolasch & Birch, LLP (57) ABSTRACT

The invention concerns an immunostimulatory and metastasis inhibiting fermented, dried vegetal material, pharmaceutical compositions containing the latter, the production process and the use of the dried material in the production dietary supplement and of immunostimulatory and metastasis inhibiting pharmaceutical compositions. The material according to the invention can be obtained by fermentation of wheat germ in an aqueous medium in the presence of Sacharomyces cerevisiae and by drying the fermented liquid.

6 Claims, 4 Drawing Sheets

IMMUNOSTIMULATORY AND METASTASIS INHIBITING FERMENTED VEGETAL MATERIAL

This application is the national phase under 35 U.S.C. § 371 of PCT International Application No. PCT/HU98/00077 which has an International filing date of Aug. 11, 1998, which designated the United States of America.

The invention relates to an immunostimulatory and metastasis inhibiting fermented and dried vegetal material, pharmaceutical compositions containing thereof, to the process for the preparation of the material and the use of the dried vegetal material as a dietary supplement and in the production of immunostimulaton, and especially metastasis inhibiting pharmaceutical compositions.

One of the main objectives of the treatment of tumours is the inhibition of metastases. The primary tumour caused by the malignant growth of the cells spreads via metastases to the neighbouring cells and organs and causes in the latter secondary tumours, which cannot be removed surgically and may also become resistant to chemotherapy.

Researchers concentrate more and more on the development of immunomodulatory materials and materials of natural—mainly of vegetable—origin have been studied intensively.

It is a well known fact that compounds with a quinone structure play an important biological role. Several quinone derivatives are to be found in plants, like ubiquinones, plastoquinones, menaquinones, which play a role in photosynthesis, but also in the cell respiratory system of vertebra, thus also humans and in the coagulation of blood etc. Several benzoquinone derivatives are also used for medicinal purposes. Adriamycin, daunorubicin and mitomycin C. are quinone derivatives with a cytostatic effect. While other benzo- and hydroquinones have an antimicrobal effect and are the active components of antibiotics suitable for treatments of bacterial infections like Tetran-B. Metacyclin and Doxycyclin.

The Literature reports that 2.6-dimethoxy-p-benzoquinone (2.6-DMBQ) and 2-methoxy-p-benzoquinone (2-MBQ) have a fungicidal and bacteriostatic effect, and that 2.6-DMBQ and 2-MBQ are also cytotoxic for malignant tumour cells. [Int. J. Quant. chem.: Quant. Biol. Symp. 7. 217–222 (1980), 9. 27–30 (1982) and 12. 257–261 (1985); Phytochemistry 27. 225 (1971) and J. Agric. Food Chem. 39. 266 (1991)]. It has been shown that a mixture of 2.6-dimethoxy-p-benzoquinone and ascorbic acid inhibits the groh of Ehrlich ascites tumour cells in mice. [Proc. Natl. Acad. Sci. USA 81. 2088–2091 (1984) and 82. 1439–1442 (1985)]. 2.6-dimethoxy-p-benzoquinone and 2-methoxy-p-benzoquinone have been found and isolated in several plants [Magy. Kem. Folyoirat 102/7. 320–325 (1996)]. These two compounds can be found in the largest quantities in glucoside form in wheat (Tricitum vulgaris), to be more exact in wheat germ. The compounds were isolated in the fifties from wheat germs fermented with yeast and identified for the purpose of examination of quality deterioration of bread to which wheat germ has been added. [Hevl. Him. Acta 33., 433 (1950); J. Chem. Soc. London 1952, 4821–4823].

According to the literature in wheat germ the quantity of 2-MBQ is about 0.05 weight %. that of 2.6-DMBQ about 0.01 weight % (as glucoside). The presence of quinones as glucosides is explained by the fact that quinones, especially) methoxy-substituted p-benzoquinones are reactive while their hydroquinone-glucosides are more stable and inert.

During our experiments relating to the stud, of the fermentation of wheat germ we concluded that the dry extract deriving from the fermented liquid produced while fermenting wheat germ with baker's yeast (Saccharomices cerevisiae) has a surprising immunostimulatory and metastasis inhibiting effect, and it can be applied successfully as the active agent of immunostimulatory and metastasis inhibiting pharmaceutical compositions.

This finding is surprising, because although the literature reports [Proc. Natl. Acad. Sci. USA 80. 129 (1983)] that a mixture of 2.6-DMBQ and ascorbic acid inhibits the growth of Ehrlich ascites tumour cells (these are eminently suitable for quantitative analysis of the growth of tumours and for the study of their biochemical functions) the extract described in the invention (which contains besides unidentifiable components 2.6-DMBQ and 2-MBQ) proved to be practically ineffective on these primary and generally all tumour cells, even when combined with ascorbic acid. It proved only very effective in the treatment of metastases. The aspects of the treatment of primary tumours and the metastases developing from the former are basically different, so it was not self-evident for the researcher that a plant extract containing components which are known to be effective in the treatment of primary tumours and not yet fully identifiable as to its chemical composition should have an immunostimulatory and metastasis inhibiting effect. [Cancer. Principles and Practice of Oncology, Vol 1.$4^{th}$ edition. J. B. Lippincott Company. Philadelphia, 1993.]

Thus the present invention concerns an immunostimulatory and metastasis inhibiting fermented and dried vegetal material which is obtainable by fermenting wheat germ with baker's yeast in an aqueous medium filtering the fermented liquid cell-free and drying it.

The present invention also relates to an immunostimulatory and metastasis inhibiting pharmaceutical composition the active agent of which contains the fermented, dried vegetal material described in the invention.

The present invention also concerns the use of the above mentioned fermented and dried vegetal material in the production of immunostimulatory and metastasis inhibiting pharmaceutical compositions.

The present invention also concerns the processes of treating mammals for the stimulation of the immune system and inhibition of metastases with the pharmaceutical composition described in the invention.

The invention further concerns a dietary supplement comprising the fermented, dried vegetal material described in the invention and maltodextrin.

According to the invention the fermented, dried societal material has been identified and examined on the basis of its 2.6-DMBQ content. We would like to note here that full identification of the chemical composition of the extract was not possible with the available methods, so all data concern the 2.6-DMBQ contents as a basis.

It proved suitable to use for the production of the fermented, dried vegetal material described in the present invention wheat germ—which is a by-product of flour milling and available in large quantities—around to flour quality, either in its original state or defatted. The use of defatted wheat germ has no specific advantages. Fermentation was done with baker's yeast (Saccharomyces cerevisiae). This type of yeast is commercially available. The period of fermentation seas about 10–24 hours, preferably 15–20 hours or about 18 hours. The temperature of the fermentation is about 25–35° C. preferably about 30° C. The weight ratio of the wheat germ and the yeast is 4:1–2:1, preferably about 3:1, the weight ratio of the dry matter and water is 1:6–1:12, preferably about 1:9.

The fermentation—on a laboratory scale—can be e.g. effected by adding in a glass fermentor to the freshly ground wheat germ the yeast suspension in water, and by stirring or shaking the mixture. The fermented liquid gets foamy.

After fermentation the mixture is centrifuged for 5–15 minutes at 2000–4500/min, preferably about 3000/min. The supernatant is boiled, cooled and dried in an appropriate manner, e. g. by lyophilisation or spray-drying.

The product, a reddish-brown powder is the material according to the invention. It is expedient to keep the material until further use cooled, and because of its hygroscopic character in sealed containers. The 2.6-DMBQ contents of the resulting dry material is about 0.4 mg/g.

In a large scale fermentation (e.g. 4 cubic meters) it is suitable to apply continuous areating, e.g. 0.5 l air/l of fermented liquid/minute, and slow stirring. The period of fermentation is about 18 hours. In order to inhibit foaming the usual additives can be applied—it is preferable to use sunflower oil. At the end of the fermentation process areating and stirring are discontinued and the fermented liquid is separated from the wheat germ—yeast suspension in the usual manner, for example in a screw decanter, subsequently in a separator and a filter press. If necessary—a filter aid material can be added. It is suitable to use 5–10 kg filtering perlite per cubic meter of fermented liquid. The fermented liquid is filtered sharp, and the quality of the filtering is checked by a microscope. The filtered fermented liquid contains practically no cells, which means that no more than 1 yeast cell is found per 10 sights. The resulting fermented liquid, Which contains about 1.5 % by weight dry material is evaporated in a vacuum condenser, preferably at a temperature of about 40–50° C. and after terminating the vacuum is boiled at atmospheric pressure for about minutes. This results in a decrease of harmful enzyme activities. Subsequently the mixture is dried by spray drying, e.g. in a rotating spray apparatus. If the above fermentation process is used the 2.6 DMBQ content of the resulting fermented, dried vegetal material is 0.12–0.52 mg/g dry material and the 2 MBQ content is 0.05–0.28 mg/g dry material—depending on the benzoquinone content of the wheat germ used.

As the final product is hygroscopic in order to enhance the effectiveness of the spray drying and the use of the final product one of the usual additives, e.g. maltodextrin, acacia gum, guar gum, xanthan, locust bean flour etc. can be used during spray drying. It is preferable to use maltodextrin. The suitable process is to determine the dry material content of the mixture evaporated in the vacuum condenser and boiled and add so much maltodextrin that the dry material content of the mixture to be dried is about 30% by weight. It is suitable to dissolve the maltodextrin in hot water and add it cooled to the condensed mixture. After drying the final product—a powder—contains about 60% by weight fermented, dried vegetal material and about 40% by weight maltodextrin.

The stability of the obtained material can be checked by monitoring the changes of the 2.6 DMBQ concentration. Quantitative analysis can be done by HPLC. The powder produced according to the above described process remains stable for about 3 years at room temperature. The fermented, dried vegetal material according to the invention can be used as the active agent of immunostimulatory and metastasis inhibiting pharmaceutical compositions. The pharmaceutical composition may also contain ascorbic acid or other cytostatic materials beside the said active agent.

The fermented, dried vegetal material can be processed to the usual solid or liquid pharmaceutical compositions for peroral or parenteral administration. During the production of the pharmaceutical compositions the hygroscopic character of the fermented, dried vegetal material must be taken into account. A suitable form is a capsule which protects the active agent from the humidity of the air.

In the production of the pharmaceutical compositions auxiliary materials usually applied in pharmaceutical practice can be used. As these materials and their possible uses are described in the pharmaceutical literature in detail, the selection and preparation of the suitable form is a routine task. The one time dosage of the effective agent can vary between wide limits depending on the state of the patient, and the selection of the suitable effective dosage must always be the responsibility of the doctor. Generally suitable results can be obtained if the dosage is 0.001–100 g, preferably 0.01–50 g, even more preferably 0.1–40 g per kg of body weight, e.g. in dosages of 0.1–10, 1–25 or 10–30 g.

The fermented, dried vegetal material according to the invention can also be mixed with ascorbic acid (Vitamin C). According to our experiments ascorbic acid may enhance the metastasis inhibiting effect of the material according to the invention. The weight ratio of the fermented, dried vegetal material and ascorbic acid can be e.g. 10:1–1:1, preferably 6:1–2:1, more preferably 3:1, 4:1 or 5:1.

The invention also concerns the immunostimulatory and/ or metastasis inhibiting treatment with the fermented, dried vegetal material according to the invention. The point of the treatment is to give the patient an effective dose of the fermented, dried vegetal material.

The fermented, dried vegetal material can also be used as a dietary supplement for mammals. In this case it is preferable to apply the mixture containing maltodextrin and the usual auxiliary materials applied in food industry, e.g. aromatic materials, sweeteners, colouring agents etc. The dietary supplement can e.g. be produced by granulating the mixture containing 60% by weight dried matter and 40% by weight maltodextrin plus aromatic materials and sweeteners in a fluid bed, and packing the instant granulate in e.g. bags.

The following examples serve to illustrate the fermented, dried vegetal material according to the invention, its production and pharmacological effects.

EXAMPLE 1

Laboratory Scale Fermentation of Wheat Germ

A suspension of 33.3 g yeast (Saccharomyces cerevisiae) and 1000 ml of drinking stealer have been added to 100 g fresh wheat germ (according to the Hungarian standard MSZ-081361-80) ground to flour quality. The mixture was shaken in a shaker for 18 hours at 30° C. During this period the fermented liquid got foamy and reached about three times its original volume. After fermentation the mixture was centrifuged for 15 minutes at 3000/min. After boiling and cooling the supernatant was dried by lyophilisation, and the resulting lyophilized matter was kept until further use in the freezer (−10° C.). The 2.6 DMBQ content of the resulting lyophilisate was 0.4 mg/g dry material (0.04% by weight).

EXAMPLE 2

Large Scale Fermentation of Wheat Germ 300 kg, wheat germ ground to flour quality (according to the Hungarian standard) and 100 kg, yeast were placed in a 5 cubic m fermentor, and drinking water was added until the volume became 4000 1. The fermentation period was 18 hours, during which continuous areating (0.5.1 air/l fermented liquid/minute) and slow stirring (30 rev./min) was used. In order to inhibit foaming 1 l/cubic m sunflower oil was added to the mixture. After fermentation areating and stirring were discontinued, and the fermented liquid was separated first in a screw decanter, then in a separator and finally in a filter press with textile filter. As auxiliary material 10 kg filtering perlite/cubic m was added. The fermented liquid was filtered sharp and the sharpness was checked be microscope. The filtered fermented liquid contained practically no cells, which meant that maximum 1 yeast cell was found per 10 sights. The resulting fermented liquid, which contained about 1.5% by weight dry material was evaporated in a vacuum condenser, at a temperature of 40–50° C. and after discontinuing the vacuum boiled at atmospheric pressure for about 15 minutes. After this the dry material content of the solution was determined and so much maltodextrin—first solved in hot water and then cooled—was added that the dry matter content of the solution became about 30 mass %. After this the solution was spray dried in a shear nozzle rotating spray drier in which the temperature of the outgoing air was 90° C. The resulting final product—a powder—contained 60% by weight of the fermented vegetal material according to the invention and 40% by weight maltodextrin. The 2.6 DMBQ content was—determined by HPLC according to the method described in the following example—0.4 mg/g dry material.

EXAMPLE 3

Characteristics of the Material According to the Invention

The material according to the invention can be characterised in two ways, either by determining its 2.6. DMBQ content or by the so-called fingerprint chromatogram. In both cases HPLC chromatography is used.

Analysis has been performed both on the material produced as described in Example 1 and on that obtained as described in Example 2, and the results were in both cases identical.

A. Quantitative and Qualitative Analysis of Benzoquinone Derivatives

Preparation of the sample

Before analysis it became necessary to increase the concentration of benzoquinones in the lyophilisate. In order to achieve this the lyophilisate was diluted to the original concentration with distilled water (1 weight % dry manner content)−(0.5 g lyophilisate, 50 ml distilled water). The solution was extracted with 3×25 ml chloroform in three steps. Eventual humidity remaining in the chloroform phase was removed with water-free Na sulphate. After filtering the chloroform phase was evaporated to the rest chloroform was added to a total volume of 5 ml. This sample was injected during the HPLC analysis.

Qualitative and quantitative analysis of the benzoquinone derivatives was performed by the HPLC method.

Description of the HPLC method

The applied HPLC equipment consists of a Beckman model 114 M pump, a LaborMim UV respectively a Merck-Hitachi-DAD mod. 4500 diode array detector, and a Waters 740 type integrator unit. A Chromsil C18 (250×4 mm) 10 $\mu$ column was used for measurements. UV detection was performed at a frequency of 290 mm, the flow rate was 2 ml/min.

The composition of the applied eluent was the following: $Na_2HPO_4$ 25 mmol. $Na_2HPO_4$ 25 mmol. $Na_2EDTA$ 25 mmol. $NH_2OH.HCl$ 20 mmol, 10 volume % methanol. pH=6.05.

Figure 1:
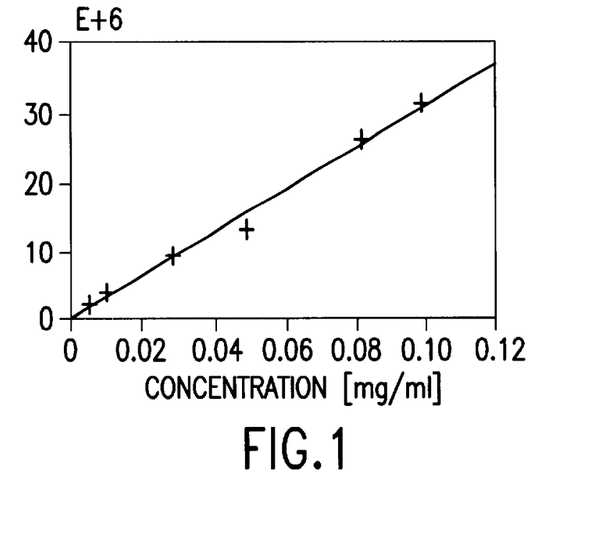
FIG. 1. Calibration diagram of the HPLC measurement of 2.6 DMBQ

Three different benzo—and hydroquinones were analyzed by the method described above. There is but a small difference between the retention time of the compounds. By decreasing the strength of the eluent—the organic phase to 10%—selectivity was enhanced to a great extent. Analysis of the retention data has shown that p-benzoquinones show a greater retention than the corresponding hydroquinones and retention increases with the number of methoxy groups. The concentration of all three standards was 0.1 mg/ml. Table 2, shows the retention times ($t_R$) of the standards and the capacity factor (k') data. The aim of the measurements was detection and quantitative definition of 2.6-dimethoxy-p-benzoquinone. So in the following this part of the measurements will be discussed in detail. It was examined whether the elaborated method is suitable for quantitative analysis of 2.6-dimethoxy-p-benzoquinone. The calibration diagram used is shown in FIG. 1. With a correlation coefficient of 0.99 the result is a straight line. It was also checked whether the measurements can be reproduced, on every sample three parallel measurements were conducted and the scattering of the results was calculated. Table 1, shows the parallel results of measurements conducted on samples during a period of six months and their scattering. Our results show that the measuring method is suitable for exact and reproducible measurement of 2.6-dimethoxy-p-benzoquinone.

TABLE 1

Parallel values of the quantitative analysis of 2.6-DMBQ and the scattering of the results

| Date | 2.6-DMBQ content (mg/50 g of sample) | | | ($\sigma$-%) |
|---|---|---|---|---|
| 04.27. | 3.45 | 3.54 | 3.66 | 0.08–2 |
| 04.28. | 3.27 | 3.68 | 3.31 | 0.18–5 |
| 05.10. | 1.56 | 1.49 | 1.48 | 0.03–1.9 |
| 05.10. | 3.65 | 3.42 | | 0.12–3 |
| 06.08. | 3.00 | 2.98 | 2.86 | 0.06–2 |
| 06.09. | 2.92 | 3.06 | 2.87 | 0.08–2.3 |
| 06.10. | 3.34 | 3.23 | 3.36 | 0.05–1.5 |

TABLE 2

Retention time ($t_R$) and capacity factor (k') values
of the examined materials

| Standard | $t_R$ | k' |
|---|---|---|
| 2.6-DMBQ | 13.4 | 5.0 |
| 2.6-DMHQ | 5.1 | 1.2 |
| 2-MBQ | 8.5 | 2.7 |

Figure 2:
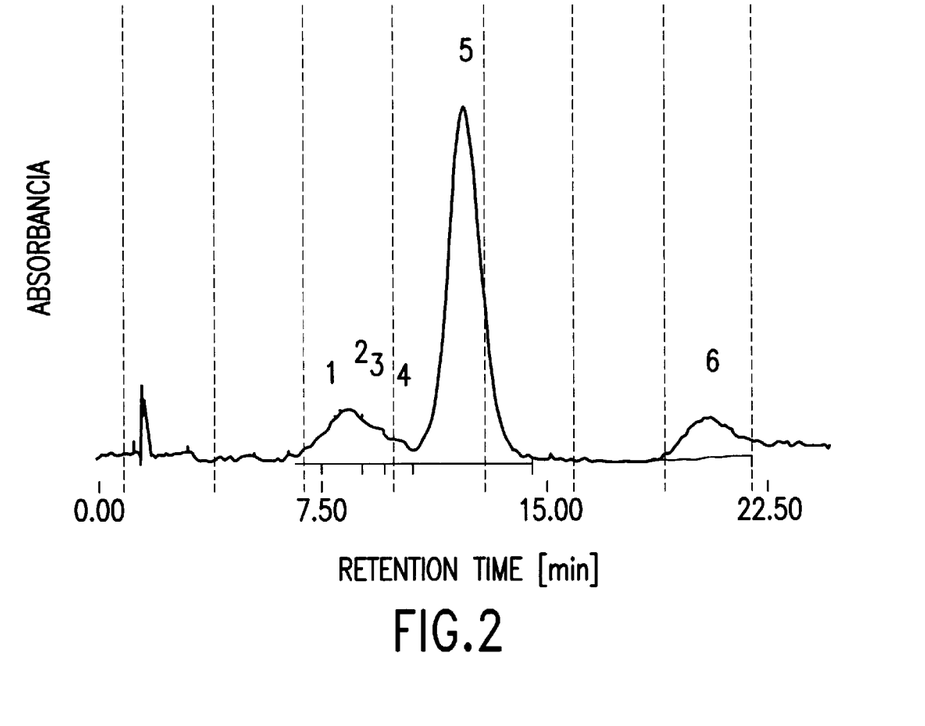
FIG. 2. HPLC chromatogram of the chloroform extract of the material

FIG. 2 shows the HPLC chromatogram of the chloroform sample prepared as described above. The chromatogram shows only one peak characteristic for 2.6 DMBQ. The 2.6 DMBQ contents of the sample was determined on the basis of the laner.

B. Fingerprint Chromatogram

Preparation of the sample 50 ml 96% of volume ethanol was added 5 g of spray dried material (prepared as described in example 2.). The mixture was shaken for 30 minutes at a temperature of 50° C. and 200/min. After this the mixture was filtered, evaporated dry and the remaining material solved in 10 ml of methanol. The filtered solution was injected onto the column.

HPLC method

The HPLC instruments column and conditions described above are used here, too, but the composition of the eluent was the following: $Na_2HPO_4$ 1.25 mmol, $NaH_2PO_4$ 1.25 mmol. $Na_2EDTA$ 1.25 mmol, $NH_2OH.HCl$ 2.50 mmol. 5 volume % methanol.

Figure 3:
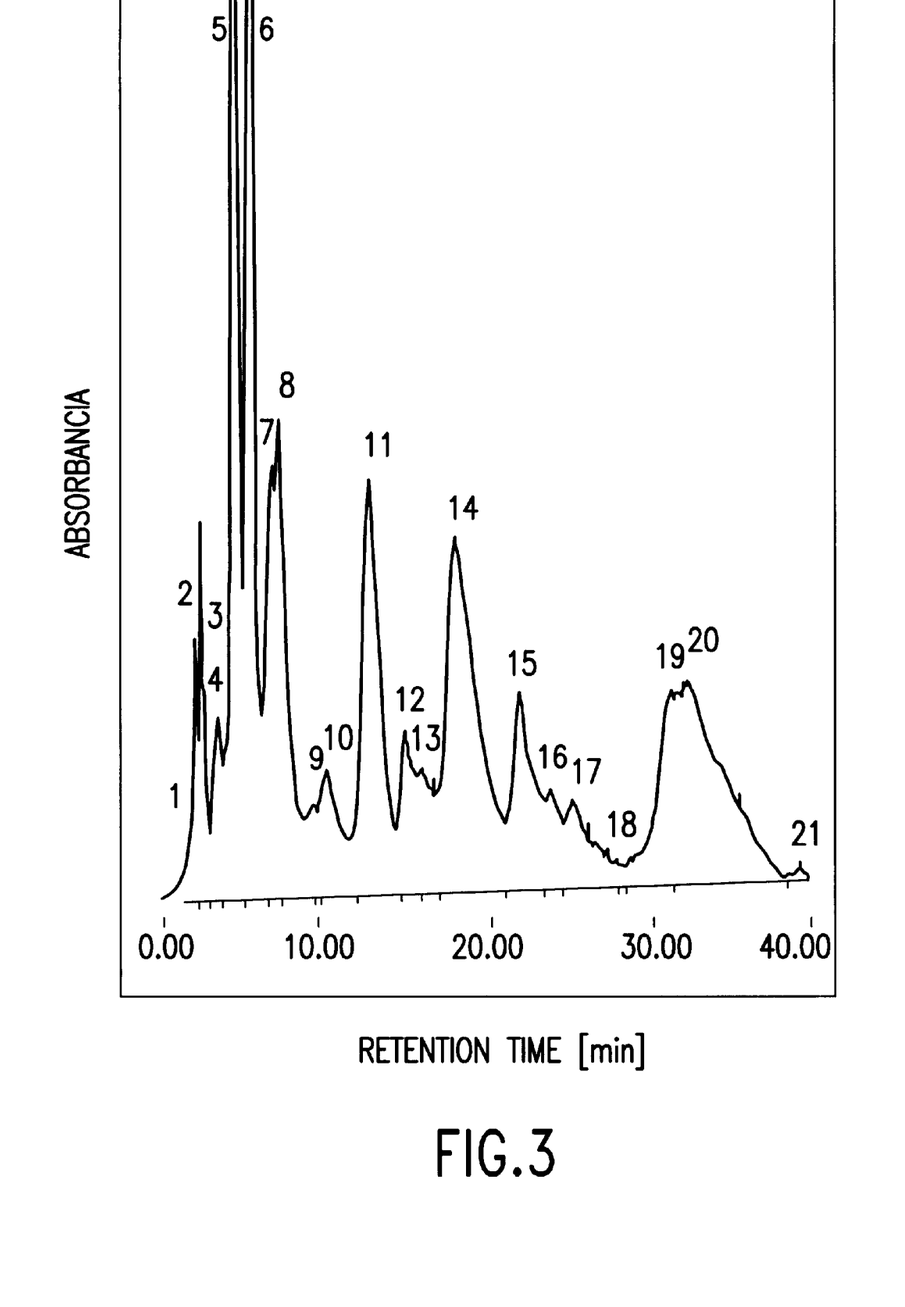
FIG. 3. HPLC chromatogram of the ethanol extract of the material

FIG. 3. shows the resulting HPLC chromatogram. It is shown that under these conditions two characteristic peaks appeared, one at about 4.7 minutes (5) and one at 5.8 minutes (6). At a retention time of 7.3. resp. 7.7 minutes two peaks (7.8) followed each other quickly, which cannot be separated completely. A peak of smaller intensity appeared at 9.8 minutes (9), followed by a characteristic intensive peak (11) at about 13.1 minutes. At about 15 minutes a smaller peak (12) and another intensive peak (14) at 18 minutes. At 21.8 minutes the chromatogram showed a smaller peak (15) and at around 31 minutes a flatter peak, containing several materials.

C. Stabilit Tests

The decomposition of the material according to the invention was checked via the chanqes in concentration of the 2.6-dimethoxy-p-benzoquinone. We conducted storage experiments at three different temperatures (room temperature 20° C. 40° C. and 60° C.) The lyophilisate—about 1 g—as stored in test-tubes which were sealed air-tight. The duration of the experiments was 8 weeks, every week three parallel measurements were conducted on samples taken from all three series kept at different temperatures. The quantitative analysis of benzoquinone derivatives was conducted by HPLC.

The tests have shown that the dried material according to the invention remained stable even after three years at room temperature, that is, the 2.6 DMBQ content remained practically unchanged. At the same time the material is not stable at 40° C.—the 2.6 DMBQ decomposes in a fetal weeks, and at 60° C. the 2.6 DMBQ contents decreases rapidly within a few days.

The decomposition of 2-methoxy-p-benzoquinone was also studied in both series of measurements. This compound is more instable than 2.6-dimethoxy-p-benzoquinone, and as a consequence its presence could not be shown after one week of storage in the samples kept at 40 or 60° C. At room temperature the concentration of this compound remained unchanged, too.

EXAMPLE 4

Tests on Effectiecness

Both the lyophilisate prepared as described in example 1, and the spray dried material prepared as described in example 2, have been tested for effectiveness. A standardised dried material was used with a 2.6 DMBQ content of 0.4 mg/g dry material and a HPLC curve as the one shown in FIG. 2. Both materials gave the same results—so the material according to the invention will be called further simply lyophilisate. Below the results of the biological and toxicological tests concerning this lyophilisate will be discussed, with a special stress on the immune reconstitution and tumour growth and metastasis inhibiting effects.

1. Tumour Growth and Metastasis Inhibiting Effect (in vivo tests)

For the tests the following injectable tumour types growing in mice or rats were used: a highly metastasis forming variant (3LL-HH) of Lewis lung carcinoma (mouse iung cancer), B16 mouse melanoma and HCR-25 human colon carcinoma xenograft.

The 3LL-HH (LLT-HH) and B16 tumours were sustained in C57Bl/6 inbred mice. The HCR-25 xenopraft was injected into CBA/CA mice, previously immunesuppressed by thymectomy and complete body irradiation. In the case of 3LL-HH and HCR-25 tumour the tumour cells were transplanted into the spleen, in the case of B16 melanoma into the muscles of the left lower extremity. A treated and a control group of the animals injected with HCR-25 tumour were also splenectomized 21 days after the transplantation of the tumour.

Treatment with he lyophilisate described in the invention was started 24 hours after injection of the tumour. Daily dosages of 3 g/body weight kg were administered per os. with a stomach probe, in the form of 0.6 g/ml aqueous suspension.

The tests were terminated 14 days after transplantation in the case of the 3LL-HH tumour, 21 days after transplantation in case of the B16 tumour and 51 days after transplantation in the case of HCR-25 5 tumour by bleeding the animals to death under narcosis.

Tables 3, 4, and 5, summarise the results of the tests.

TABLE 3

Effect of treatment with the lyophilisate according to the invention on the number of liver metastases in case of 3LL-HH mouse lung cancer injected into the spleen

| Treatment | Number of injected cells | Number of liver metastases |
|---|---|---|
| Control | $3 \times 10^3$ | 104.0 ± 28.2 |
| Lyophilisate | $3 \times 10^3$ | 29.8 ± 16.4* |

$p < 0.01$
every test group contained 10 animals

TABLE 4

Effect of treatment with the lyophilisate according to the invention on the number of liver metastases 51 days after the HCR-25 human colon carcinoma had been injected into the spleen of immunesuppressed CBA/CA mice

| Treatment | Weight of spleen with tumour (g) | Number of liver metastases |
|---|---|---|
| Control, non-splenectomized | 1.02 ± 0.59 | 42.0 ± 25.8 |
| Lyophilisate, non-splenectomized | 0.62 ± 0.47 | 19.5 ± 19.0 |

TABLE 4-continued

Effect of treatment with the lyophilisate according to
the invention on the number of liver metastases 51 days
after the HCR-25 human colon carcinoma had been injected
into the spleen of immunesuppressed CBA/CA mice

| Treatment | Weight of spleen with tumour (g) | Number of liver metastases |
|---|---|---|
| Control, splenectomized* | 0.10 ± 0.02 | 19.1 ± 13.5 |
| Lyophilisate splenectomized* | 0.08 ± 0.02 | 10.6 ± 11.6 |

*Splenectomy was performed 21 days after the tumour had been injected onto the spleen
Every test group contained 12 animals

TABLE 5

Effect of treatment with the lyophilisate according to
the invention on the weight of the extremity injected
with the tumour and on the number of lung metastases in
the case of B16 melanoma injected into the muscles of
the extremity 21 days after the tumour had been injected

| Treatment | Weight of the extremity with tumour (average) | Number of lung metastases (average) |
|---|---|---|
| Control | 7.6 ± 0.43 | 42.4 ± 10.2 |
| Lyophilisate | 7.2 ± 0.38 | 6.2 ± 3.7* |

*p < 0.01
every test group contained 10 animals

The above results show that treatment with the lyophilisate described in the invention decreased significantly—by 71%—the number of lung metastases when 3LL-HH tumour had been injected into the spleen. (Table 3.)

In case of HCR-25 human colon carcinoma the 50 day treatment decreased both the weight of the spleen with tumour and the number of liver metastases. The number of metastases as compared to the control group was about 50% both in the splenectomized and in the non-splenectomized groups. (Table 4.)

In case of B16 melanoma injected into the muscle the weight of the tumour growing in the muscle did not change as an effect of the treatment, but the number of lung metastases decreased very significantly, by 85% as compared to the control group (Table 5.)

II. In Vitro Tests

As the above tests have shown unambiguously that the lyophilisate described in the invention can decrease significantly metastases of malignant tumours, the effects of the products on the different phases of the forming of metastases were also examined. The forming of metastases consists of several phases, in which besides the proliferation and apoptotic activity of the cells of the primary tumour, the adhesion potential of the tumour cells and the protective mechanisms of the organism aeainst the tumour cells play a role. In the in vitro tests the effect of the lyophilisate on cell proliferation and apoptosis and adhesion were studied.

As a great part of the in vivo tests was performed on B16 mouse melanoma cells, in the first step this tumour was used to test the lyophilisate.

1. Adhesion Test

Figure 4:
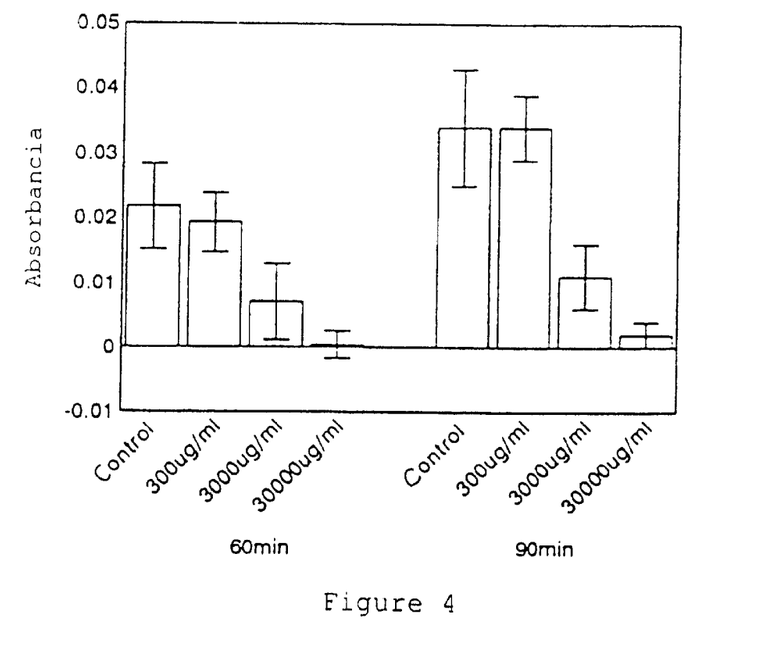
FIG. 4. Binding of B16 tumour cells in the presence of lyophilisate of different concentrations in the 60th and 90th minute after placing. (Every value represents the average of 8 parallel measurements±SD, evaluation by spectrophotometric measurement)

The adhesion of the tumour cells was tested on a 96-hole microplate. The dosages of the lyophilisate were 300, 3000 and 30000 µg/ml. RPMI culture-medium was used, both in the absence of serum and in the presence of 10% FCS. The adhesion was tested 10, 30, 60, 90 and 120 minutes after incubation in usual circumstances. Evaluation was performed by colorimetry process on the basis of the SRB assay.(Mossmann. T.: 3. lmmunol. Neth. 65, 55–63/1983/). The test is based on sulforhodamine B-colouring of the total protein content of the culture, absorbency was read at 570 nm with a spectrophotometer. FIG. 4. only shows two moments in time, which, however represent the effect of the lyophilisate adequately. It was shown that if the dosage of the lyophilisate was 3000 µg/ml or ten times higher, it decreased the adhesion of tumour cells dramatically, both in the presence and absence of serum. If the dosage is 300 µg/ml, no such effect can be observed.

2. Proliferation Test

Figure 5:
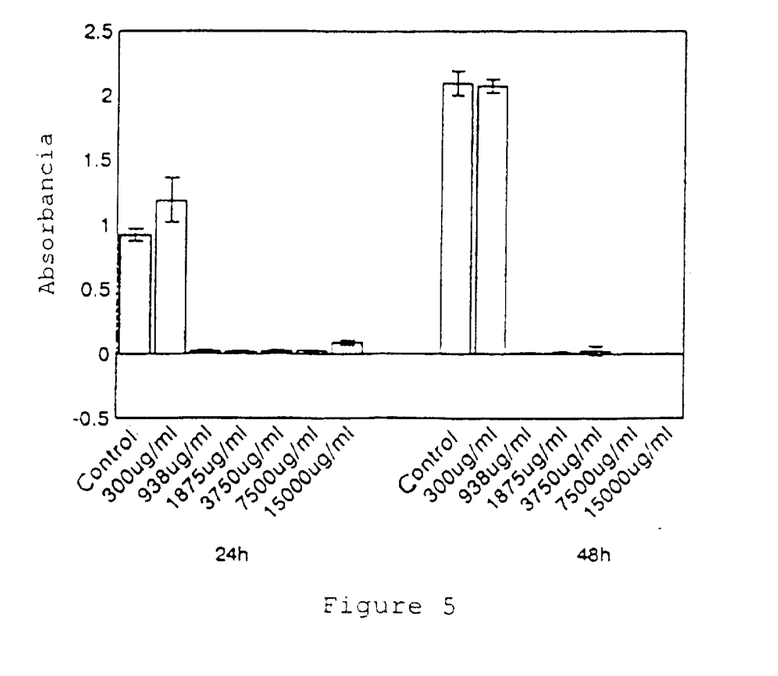
FIG. 5. The effect of different dosages of lyophilisate on the proliferation of B16 cells after 24 and 48 hours after the commencement of the treatment. (Every value represents the average of 8 parallel measurements±SD, evaluation by spectrophotometric measurement)

In this test the tumour cells were placed 24 hours before treatment on the 96-hole microplate. After treatment with appropriate dosages of the lyophilisate the proliferation activity of the cells was also tested by the SRB assays, 24, 48 and 72 hours after treatment. The results of the repeated tests have shown that as effect of the treatment in the 900–15 000 µg/ml rangle the tumour cells come to the surface of the monolayer and—as shown by the trypan-blue dye exclusion method—died. (Kaltenbach. J. P. et al.: Exp. Cell Res. 15, 112–217/1985/). (FIG. 5.)

Figure 6:
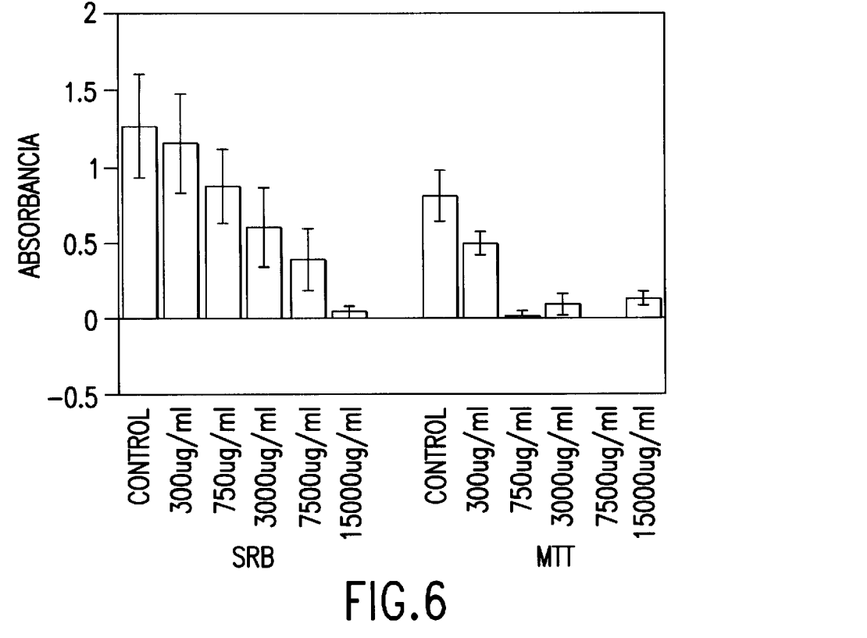
FIG. 6. The development of A2058 human melanoma in the presence of different dosages of lyophilisate 24 hours after the commencement of the treatment. The evaluation of the cultures was performed on the basis of protein (SRB) and dehydrogenase activity (MTT) by parallel spectrophotometric measurements. (Even value represents the average of 8 parallel measurements±SD)
Figure 7:
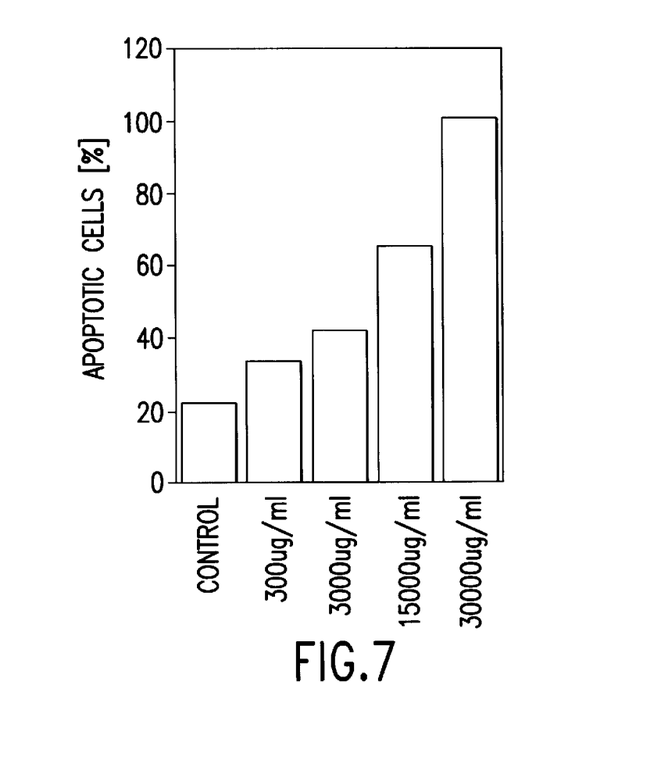
FIG. 7. Ration of apoptotic cells (FACS analysis) in the A2058 human melanoma in vitro cultures after treatment With different dosages of the lyophilisate.

Our tests on human amelanotic melanoma (A2058 tumour cells—Todaro, G. J. et al.: Proc. Natl. Acad. Sci. USA 77, 5258–5262/1980/) have shown similar results to those on mouse melanotic melanoma (FIG. 6.) In the case of this tumour parallel to the SRB assay the MTT assay representing the metabolic activity of the cell was also performed (Cole, S. P. C.: Cancer Chemother. Pharmacol. 17, 29–263/1986/). The test is based on the phenomenon that a metabolically, active cell transforms tetrasolium salt into a coloured formazan product, primarily via its dehydrogenase activity. The colour reaction, which is proportional to the activity, can be read by a spectrophotometer at 570 nm, the MTT assay has shown clearly that functional activity of the tumour cells decreased even if the dosage was 300 µg/ml (FIG. 4.). As in case of the cells come to the surface the cause of apoptosis was unknown, the apoptotic activity of the complete cell population was tested by flow cytometric (FACS) analysis (FIG. 7.). As FIG. 7 shows the tumour cells were in apoptosis—depending on the dosage—to an unusually great extent.

III. Test of Effects on Immune Reaction

The effect of the lyophilisate described in the invention was examined in two different models. In one series of tests the possibility of blast transformation of mononuclear cells gained from the spleen of animals treated with the lyophilisate was studied, while in the others in the allograft skin transplantation model the total binding of skin transplanted in the back region of mice was studied.

1. Test of Blast Transformation of T-lymphocytes

Treatment with the lyophilisate described in the invention significantly increases blast transplantation of the T-lymphoctes playing an important role in immune reaction. This was shown by the following experiment.

$C_{57}Bl_{16}$ mice were treated for six weeks five times per week per os. with a stomach probe with the lyophilisate described in the invention in a 3 g/kg dosage (0.6 g/ml aqueous suspension). After completion of the treatment the lymphocytes gained by perfusion from the spleen of the animals were transferred into a cell culture, treated with 1 µg/ml Con A. After 48 hours the cells performing DNS synthesis were marked by 0.4 µCi $^3$H timidin. The decree of marking was defined with a liquid scintillation counter. (Beckman). As Table 6, shows treatment with Con A significantly increased—as compared to the control—the incorporation of $^3$H-TdR, that is, blast transformation.

TABLE 6

Incorporation of $^3$H-timidin into the spleen lymphocytes of the control and lyophilisate treated mice

| Treatment | 1 µg/ml ConA | |
|---|---|---|
| | average (cpm) | SEM |
| Control | 3760.6 | 583.3 |
| Lyophilisate | 8041.8 | 957.1 |

2. Test of Immunostimulator Effect in the Allograft Skin Transplantation Model The best model for the illustration of the restitution of deficient immune reaction is the allograft skin transplantation test in mice made partdy immune deficient by thymectomy (operational removal of the thymus). The $C_{57}Bl_{10}$ and $B_{10}LP$ mouse stocks only differ in the H-3 locus, so the skin transplanted from members of one stock onto the other is not rejected within 7 days, but only after about 3 weeks. If the recipient had been thymectomized, rejection occurs after an average of 50 days. All materials which advance the ripening and differentiating of the lymphocytes of the medulla, like the hormones of the thymus, decrease the time necessary for rejection of the transplanted skain. (J. Immunpharmacology 7, 67–78/1985/). The same effect could be observed in our tests when treatment with the lyophilisate described in the invention was applied.

$C_{57}Bl_{10}$ mice were used as recipient, and $B_{10}LP$ mice as donor. The recipient mice were thymectomized and skin transplantation followed after 7 weeks. Per os –5 times per week, 30 mg/kg—treatments with the lyophilisate were stared one week after thymectomy. Treatment was concluded 70 days after skin transplantation. Eventual rejection of the skin was observed daily. Table 7 shows that rejection time in non-thymectomized mice was 21 (males) resp. 28.7 (females) davs. In thymectomized mice rejection time was lengthened to 52.4 resp. 41.6 days. Treatment with the lyophilisate according to the invention shortened significantly in thymectomized and treated mice the survival of the skin transplants (grafts). This shows that immune deficiency caused by thymectomy was reduced signlficantly as a result of the treatment, which means that the lyophilisate has an immune stimulant effect.

TABLE 7

The effect of treatment with the lyophilisate according to the invention on the rejection of skin grafts (recipient $C_{57}Bl_{10}$ mice, donor $B_{10}LP$ mice)

| | Rejection time | | | |
|---|---|---|---|---|
| Treatment | average (days) | Male SEM | average (days) | Female SEM |
| Control (non-thymectomized) | 21.0 | 3.1 | 28.7 | 4.5 |
| Control (thymectomized) | 52.4 | 5.0 | 41.6 | 5.5 |
| Lyophilisate (30 mg/kg) | 28.8* | 8.6 | 32.6** | 4.5 |

*0.001 < p < 0.01 vs thymectomized control
**0.01 < p < 0.05 vs thymectomized control In vivo and in vitro tests with the lyophilisate according to the invention show that this product has a significant antimetastatic effect in several animal test models. This effect is probably connected to the immunostimulator, effect observed both in the in vivo and in vitro tests, but it is possible that the decrease in the number of metastases is also influenced by the antiproliferative, apoptosis causing effects, the effect of the material on adhesion and the effect causing the creation of free radicals.

IV. Test of Radical Binding Activity

As benzoquinones have got a well-known effect on the forming of free radicals, the radical binding activity, of the lyophilisate described in the invention was also tested. Both the superoxide (SSA) and hydroxyl radical binding (OH-SA) were measured with the electron spin resonance method. The lyophilisate has a significant SSA, the clean radical bindings activity of 1 mg corresponds to the activity of 5.64 µg superoxide dismutase (SOD). The lyophilisate has no OH-SA activity, but it disrupts the hydrogen-peroxide/Fe hydroxyl radical forming system, so it can be supposed that it has so-called non-chelator activity.

V. Toxicological Tests (Subacute)

The 77 day toxicological tests were performed according to the recommendations of the Registry of Industrial Toxicology Animal-data (RITA). (Exp. Toxic. Pathol. 47, 247–266/1995/) on F344 rats and $C_{57}Bl_{16}$ mice. The animals were treated daily with a dosage of 3 g/kg (0.6 g/ml aqueous suspension). During treatment the changes of weight of the animals, eventual pathological physical changes, spontaneous perishing of the animals were observed. On concluding the test the weight of the heart, lungs, thymus, spleen, liver, kidneys and testicles were measured and the 34 organs prescribed by the RITA were pathologically examined. No spontaneous perishing was observed, the weight of the animals changed like that of the control group. On conclusion of the test the weight of the different organs showed no changes as compared to the control group. During pathological processing of the treated animals no changes were observed, which could have been caused by the lyophilisate.

The above results show that the fermented vegetal material according to the invention is not toxic, and because of its immunostimulatory effect it is indicated in all states in which the irmune system is damaged. Because of its above described biological characteristics it can have its complementary uses in the medical treatment of malignant tumours, mainly in the inhibition of metastases.

What is claimed is:

1. A process for producing an immunostimulatory and metastasis inhibiting fermented, dried material wherein ground wheat germ is fermented in an aqueous medium in the presence of Sacchromyces cerevisiae and the fermented liquid is separated, fine filtered, evaporated, boiled and dried.

2. The process according to claim 1, wherein the fermentation is carried out at a temperature of about 30° C. for about 18 hours under continuous areating and stirring.

3. The process according to claim 2, wherein the drying is performed in the presence of maltodextrin.

4. A process according to claim 1, wherein the liquid is dried in the presence of auxiliary drying materials.

5. A method for the production of an immunostimulatory and metastasis inhibiting pharmaceutical composition wherein ground wheat germ is fermented in an aqueous medium in the presence of Saccharomyces cerevisiae and the fermented liquid is separated, fine filtered, evaporated, boiled, dried and added to a pharmaceutically acceptable carrier.

6. A method for the production of a dietary supplement for mammals wherein ground wheat germ is fermented in an aqueous medium in the presence of Saccharomyces cerevisiae and the fermented liquid is separated, fine filtered, evaporated, boiled and dried and adding the dried composition to an auxiliary material applied in the food industry.

* * * * *

UNITED STATES PATENT AND TRADEMARK OFFICE
CERTIFICATE OF CORRECTION

PATENT NO.    : 6,355,474 B1
DATED         : March 12, 2002
INVENTOR(S)   : Mate Hidvegi et al.

It is certified that error appears in the above-identified patent and that said Letters Patent is hereby corrected as shown below:

<u>Title page,</u>
Item "[22] PCT Filed:", please correct the date from "Aug. 13, 1998" to
-- Aug. 11, 1998 --.

Signed and Sealed this

Twenty-fifth Day of June, 2002

Attest:

Attesting Officer

JAMES E. ROGAN
*Director of the United States Patent and Trademark Office*